United States Patent
Regnier et al.

(10) Patent No.: US 11,364,365 B2
(45) Date of Patent: Jun. 21, 2022

(54) DELIVERY SYSTEM WITH AN OPERATING HANDLE CONTROLLING A STEERABLE CATHETER FOR THE IMPLANTATION OF A LEADLESS CARDIAC CAPSULE

(71) Applicant: CAIRDAC, Antony (FR)

(72) Inventors: Willy Regnier, Longjumeau (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 238 days.

(21) Appl. No.: 16/416,201

(22) Filed: May 18, 2019

(65) Prior Publication Data
US 2020/0360664 A1 Nov. 19, 2020

(51) Int. Cl.
| | |
|---|---|
| A61B 17/34 | (2006.01) |
| A61M 25/01 | (2006.01) |
| A61N 1/362 | (2006.01) |
| A61N 1/375 | (2006.01) |
| A61B 17/00 | (2006.01) |
| A61N 1/05 | (2006.01) |

(52) U.S. Cl.
CPC ..... *A61M 25/0136* (2013.01); *A61B 17/3468* (2013.01); *A61N 1/362* (2013.01); *A61N 1/3756* (2013.01); *A61B 2017/0042* (2013.01); *A61B 2017/00323* (2013.01); *A61B 2017/00367* (2013.01); *A61M 25/0147* (2013.01); *A61N 1/0573* (2013.01)

(58) Field of Classification Search
CPC ...... A61B 17/3468; A61B 2017/00323; A61B 2017/00336; A61B 2017/00367; A61B 2017/00389; A61B 2017/0042; A61B 2217/007; A61B 5/318; A61B 5/6861; A61B 2017/347; A61B 2017/00327; A61B 2017/00371; A61B 5/686; A61M 25/0136–0147; A61N 1/0573; A61N 1/362; A61N 1/372; A61N 1/37205; A61N 1/3756
See application file for complete search history.

(56) References Cited

U.S. PATENT DOCUMENTS

| | | | |
|---|---|---|---|
| 2003/0120290 A1* | 6/2003 | Danitz | A61B 17/122 606/151 |
| 2014/0378991 A1 | 12/2014 | Ollivier | |
| 2016/0339207 A1* | 11/2016 | Beeckler | A61M 25/0136 |
| 2017/0143980 A1* | 5/2017 | Soltis | A61B 17/3468 |
| 2020/0094020 A1* | 3/2020 | Appling | A61M 25/0147 |

* cited by examiner

*Primary Examiner* — Wade Miles
*Assistant Examiner* — Mohammed S Adam
(74) *Attorney, Agent, or Firm* — CRGO Global; Steven M. Greenberg

(57) ABSTRACT

The bending of the catheter is controlled from the handle by a variable tension exerted to a steering cable housed in an offset longitudinal notch of the catheter. The handle comprises: a body adapted to be held in hand by an operator; a piston, axially mobile in rotation and in translation inside the handle body; a first mechanism with a pulley for the winding of the steering cable and a lever for modifying in a controlled manner the tension of the cable and hence controlling the steering of the catheter; and a second mechanism comprising a member for holding a security wire and a member for adjusting the axial position of this wire with respect to the internal tube of the catheter, so as to keep the security wire in tight condition whatever the bend provided to the catheter by operation of the first mechanism.

13 Claims, 6 Drawing Sheets

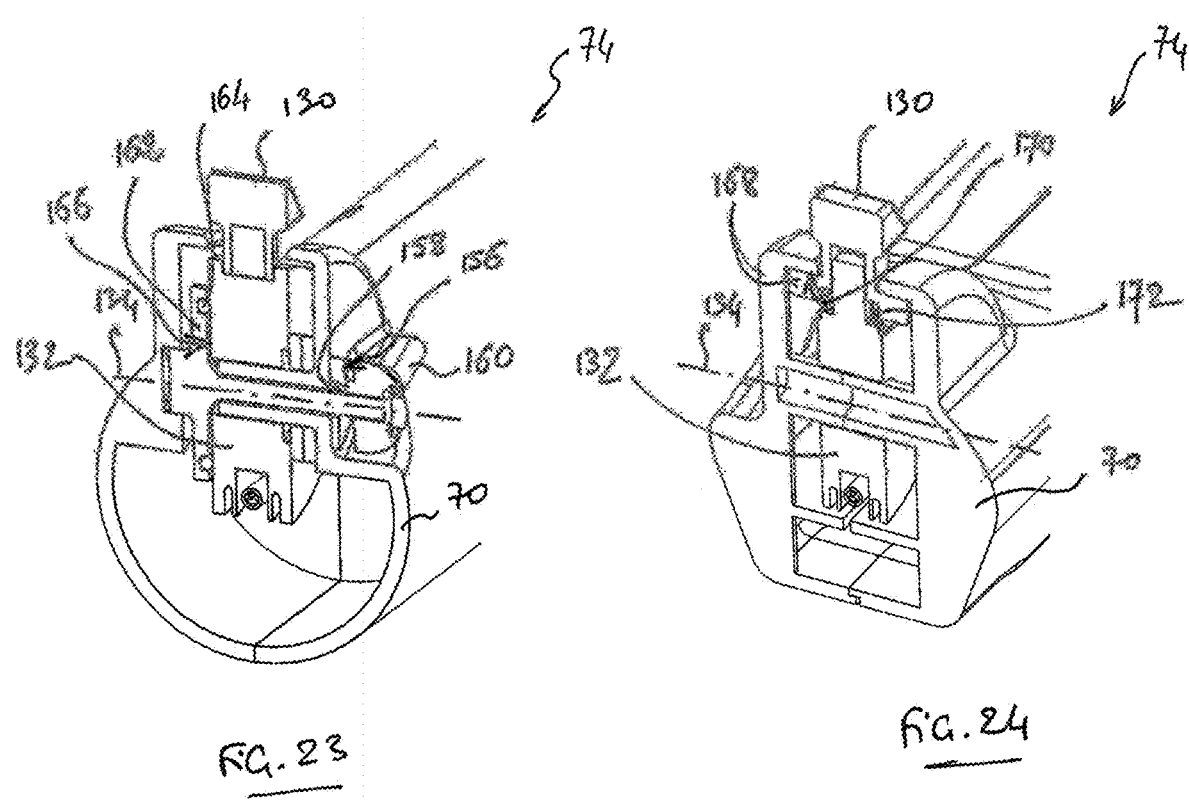

DELIVERY SYSTEM WITH AN OPERATING HANDLE CONTROLLING A STEERABLE CATHETER FOR THE IMPLANTATION OF A LEADLESS CARDIAC CAPSULE

BACKGROUND OF THE INVENTION

Field of the Invention

The invention relates to tools for implanting (or "delivering") implantable medical devices, i.e. tools for positioning a device at a chosen implantation site in the organism of a patient.

The invention more particularly relates to the accessories for implanting a device of the autonomous implantable capsule type.

Such a device, hereinafter referred to as "autonomous capsule", "leadless capsule" or simply "capsule" is in the form of a capsule implanted in a heart chamber (ventricle, atrium or even arterial left heart chamber). The capsule is autonomous, i.e. it is devoid of any physical connection to a main device, the latter being implanted (such as a stimulation pulse generator box) or not implanted (external peripheral such as a programmer or a monitoring device for the remote follow-up of the patient). For that reason, such type of device is said "leadless", to distinguish it from the electrodes or sensors arranged at the distal end of a conventional lead, along the whole length of which run one or several conductors galvanically connecting the electrode or the sensor to a generator connected to an opposite, proximal end of the lead.

In this case of a cardiac application, the leadless capsule continuously monitors the patient's cardiac rhythm and, if necessary, issues to the heart electrical pulses for stimulation, resynchronization and/or defibrillation in case of rhythm disorders detected by the capsule. The capsule may be an epicardial capsule fixed to the outer wall of the heart, or an endocavitary capsule fixed to the internal wall of a ventricular or atrial cavity, or also a capsule fixed to the wall of a vessel near the myocardium.

The invention is however not limited to the implantation of a particular type of capsule, nor even of leadless implant; it is applicable as well to many other types of implantable medical devices, whatever the operational purpose thereof, cardiac or other, for example to capsules adapted to diffuse in situ an active pharmacological agent.

Description of the Related Art

US 2009/0171408 A1 (Solem), US 2017/0151429 A1 (Regnier) and WO 2018/122244 A1 (Regnier) describe various examples of intracardiac leadless capsules.

The capsules comprise various electronic circuits, sensors, etc., as well as wireless communication transceiver means for the remote exchange of data, the whole being integrated into a body of very small size that can be implanted at sites whose access is difficult or that leave little space available, such as the apex of the ventricle, the internal wall of the atrium, etc. For their fastening in situ at the implantation site, these capsules are provided at their distal end with an anchoring member adapted to enter the tissues of a body wall. A typical example of such an anchoring member comprises a protruding helical screw axially extending the capsule body and adapted to enter the cardiac tissue by being screwed thereinto at the implantation site. There exist other types of anchoring members, with, for example, pins, hooks, fins, etc., penetrating the tissues to permanently secure the medical device thereto.

The implantation of endocavitary leadless capsules (i.e. capsules to be fastened to the internal wall of a ventricular or atrial chamber, as opposed to the epicardial capsules, fixed to the outer wall of the heart) entails significant implantation constraints, in particular due to the approach way that requires passing through the peripheral venous network.

Indeed, due to the relatively large dimensions of present leadless capsules, which have a typical diameter of about 4 to 7 mm for a length of 15 to 40 mm, with an object of such a size there exists no upper-way procedure, i.e. via the subclavian vein, to accede to a heart chamber, in particular to reach the bottom of the right ventricle. It is hence necessary to use a different access, starting from a femoral puncture site, then going along the inferior vena cava up to the heart.

Such a femoral access is more complex, in particular due to the significant angulation between the inferior vena cava and the axis of the right ventricle. In the case of an upper-way access, when arriving into the atrium, the distal portion of the implantation catheter is naturally directed towards the apex of the right ventricle, and it is just necessary to push on the catheter to pass through the tricuspid valve and to reach the bottom of the ventricle, into which the anchoring member will be screwed after having docked to the wall. On the other hand, in the case of a femoral access, once the atrium reached, it is necessary to operate a tilting of the distal end of the catheter to direct this end towards the ventricle and to allow it to pass through the tricuspid valve and to continue its progression in the good direction, towards the bottom of the ventricle.

There exist for that purpose steerable catheters, which are well-known implantation tools whose distal end is operable from a handle located at the opposite end, on the proximal side, so that such a steering operation can be performed, under an image intensifier, in the atrium.

Such a steerable catheter and the way to operate the implantation are described in particular in US 2014/0378991 (Ollivier). The implantation tool disclosed by this document further comprises a cylindrical protective tip extending the steerable catheter at its distal portion and containing the capsule to be implanted. This capsule is coupled to a sub-catheter (or "delivery catheter") inserted into the central internal lumen of the main catheter (or "guide catheter"), and is maintained in retracted position in the tip for the whole duration of the approaching operation. The capsule and the delivery catheter are temporarily connected through a simple disengageable mechanism allowing a complete screwing of the capsule into the heart wall, then the final release thereof. The telescopic configuration of the delivery catheter allows ejecting the capsule out of the protective tip and beyond the latter over several centimetres, making it possible in any circumstance to fully and accurately bring the capsule to the bottom of the ventricle.

The guide catheter is operated by the practitioner by means of a suitable handle comprising a mechanism comparable to that described in U.S. Pat. No. 5,891,088 (Thompson et al.) and U.S. Pat. No. 5,462,527 (Stevens-Wright et al.). More particularly, the guide catheter contains, in its structure, an elastically deformable external tube, receiving the delivery catheter, with, in the thickness of this external tube, two diametrically opposed lumens in which a cable extends freely from one end of the catheter to the other. At their proximal end, the cables are connected to a mobile part incorporated to the handle and whose displacement is controlled by the practitioner, for example by means of levers at his/her disposal on the handle. The operation consists in exerting through these means a different traction on the two diametrically opposed cables so as to tighten one cable more strongly than the other: the so-exerted differential constraint results in bending the elastically deformable tube, and hence the guide catheter, to the more tightened cable side. Moreover, as the deformable tube has a variable stiffness along its length, for example more flexible in its distal portion (to-be-implanted capsule side) and more rigid in its proximal region (handle side), the bend will be essentially formed in the region of the guide catheter distal end, i.e. where the tip containing the capsule to be directed has to be steered towards the target implantation site.

One of the drawbacks of this implantation material is the large overall diameter of the guide catheter, due to its thickness that must be sufficient to form therein the two diametrically opposed lumens into which will slide the operating cables. To this thickness is to be added that of the delivery catheter itself (the telescopic catheter mobile within the guide catheter, carrying the capsule to be extended and screwed) as well as that of the external protective sheath of the guide catheter. Moreover, a sufficient clearance must be provided between the guide catheter and the delivery catheter, not only to allow the free sliding and the free rotation of the delivery catheter within the guide catheter, but also to allow the circulation with a sufficient flow rate of a flushing liquid during the whole duration of the implantation operation. The flushing liquid is injected from the handle into one of the internal lumens of the delivery catheter, up to the implantation region.

In practice, for a diameter of the order of 0.4 mm for the two lumens for the passage of the cables, formed in the thickness of the guide catheter, and taking into account the sufficient clearance that must be left between the delivery catheter and the guide catheter, the typical overall diameter of the current guide catheters of this type is never lower than 18 French, i.e. 6 mm.

This lead to guide catheters of relatively large diameter, which it is difficult to introduce and to make progress over the whole length of the peripheral venous network from the femoral puncture site to the heart.

To remedy this drawback, it has been proposed, as disclosed in U.S. application Ser. No. 16/237,749 filed on Jan. 1, 2019 and assigned to the present applicant, hereby incorporated by reference, a new structure of steerable catheter having an overall diameter substantially reduced with respect to tools currently at the disposal of the practitioners, and that with equal performances, i.e. with identical or even increased possibilities of controlling the bending during the implantation procedure, and of free circulation of the flushing fluid during the whole duration of the operation. In this structure, the mobile tube and the intermediate tube are coaxial to each other, extend from a proximal end to a distal end of the steerable catheter and are mounted telescopically into each other with possibilities of mutual rotation and mutual axial translation.

The mobile tube comprises at least one central lumen located in the vicinity of the catheter axis, extending axially from the proximal end to the distal end, and in particular adapted for the passage a security wire or "Ariadne's thread" connecting in any circumstance the capsule to the handle held by the practitioner. The intermediate tube comprises over its whole length a longitudinal notch radially offset in a direction of offset with respect to the axis of the steerable catheter and extending axially from the proximal end to the distal end. The longitudinal notch contains a cable adapted to undergo a traction exerted from the proximal end, adapted to generate a bending of the steerable catheter (towards the offset direction of the notch housing the cable). The catheter further comprises a sealed external sheath surrounding the intermediate tube over its periphery and covering the longitudinal notch over its length.

BRIEF SUMMARY OF THE INVENTION

The present invention relates to an implantation tool specifically dedicated to the operation of such a steerable catheter, the tool comprising in particular, at the proximal end of the catheter, an operating handle at the disposal of the practitioner to perform the different operations of the sequence of implantation.

Indeed, with such a catheter, it is not possible to use conventional operating handles (such as those described in above-mentioned U.S. Pat. Nos. 5,891,088 and 5,462,527) due to the absence of differential steering mechanism: because of the specific structure of the catheter, the bending of the distal end in a given plane actually results from the controlled traction of a single cable and not from the relative displacement of a pair of cables operated in opposition, as in conventional catheters.

For operating the particular catheter exposed hereinabove, the operating handle of the tool of the invention comprises: a handle body adapted to be held in hand by an operator, the handle body being coupled to the external tube of the catheter; a piston, axially mobile in rotation and in translation inside the handle body, and coupled in rotation and in translation to the internal tube of the catheter; and a first control mechanism, comprising a pulley for winding the at least one steering cable and a bending actuator operable to control a rotation of the pulley to modify in a controlled manner the tension of the steering cable whereby controlling the steering of the catheter.

According to various subsidiary features:
the handle further comprises a second control mechanism, comprising a member for holding the security wire and a member for adjusting a relative axial position of the security wire with respect to the internal tube of the catheter, whereby keeping the security wire in a tight condition whatever a bend given to the catheter by operating the first control mechanism;
the second control mechanism comprises a slider mobile in translation inside the piston, comprising at its distal end a device for fastening it to the proximal end of the catheter internal tube, and further comprising a device for adjusting the axial position of the slider inside the piston. This adjustment device may comprise, in particular, a threaded rod and a wheel mobile in axial rotation with respect to the piston, the wheel comprising a threaded bore into which is mounted the threaded rod, in particular with the slider, the threaded rod and the wheel mounted coaxial to each other and passed through by a common axial orifice opening on the proximal side of the handle and from which emerges a portion of the security wire extending beyond the operating handle;
the security wire holding member is located at the exit of the common axial orifice, on the proximal side of the handle;
the handle further comprises an axial backlash compensation device between the slider and the piston;
the first control mechanism further comprises a mechanism for locking the rotational position of the winding pulley, and a device for blocking/unblocking the locking device, adapted to be controlled by an external action from the operator, and maintained in blocked position in an absence of external action from the operator;

the handle further comprises a mechanism for indexing the rotational position of the winding pulley controlled by the bending actuator; the first control mechanism comprising the winding pulley and the bending actuator is arranged on the distal side of the handle body, and the second control mechanism, comprising the security wire holding and adjustment members, is arranged on the proximal side of the handle body, and the piston comprises, at its proximal end, an operating button protruding from the handle body on the proximal side of the handle body;

the handle further comprises at least one access pathway in fluid communication with the inside of the catheter for the circulation of a flushing liquid along a catheter flushing pathway comprising the at least one central lumen; and/or the handle further comprises a mechanism for rotationally blocking the piston with respect to the handle body, the blocking mechanism being adapted to be actuated by a control member at the disposal of an operator of the handle and being operational between a blocking configuration, in an absence of external action exerted by the operator, and an unblocking configuration, under an external action exerted by the operator.

BRIEF DESCRIPTION OF THE DRAWINGS

The foregoing and other objects, aspects and advantages of the invention will be better understood from the following detailed description of a preferred embodiment of the invention with reference to the appended drawings, in which the same numerals refer to identical or functionally similar features over the different figures.

FIG. 23 is a sectional cavalier perspective view, taken at the distal part of the handle, illustrating a third exemplary embodiment of the device for blocking the bending actuator in position.

FIG. 24 is a sectional cavalier perspective view, taken at the distal part of the handle, illustrating a fourth exemplary embodiment of the device for blocking the bending actuator in position.

DETAILED DESCRIPTION OF A PREFERRED EMBODIMENT OF THE INVENTION

An exemplary embodiment of the invention will now be described with reference to the drawings.

Figure 1:
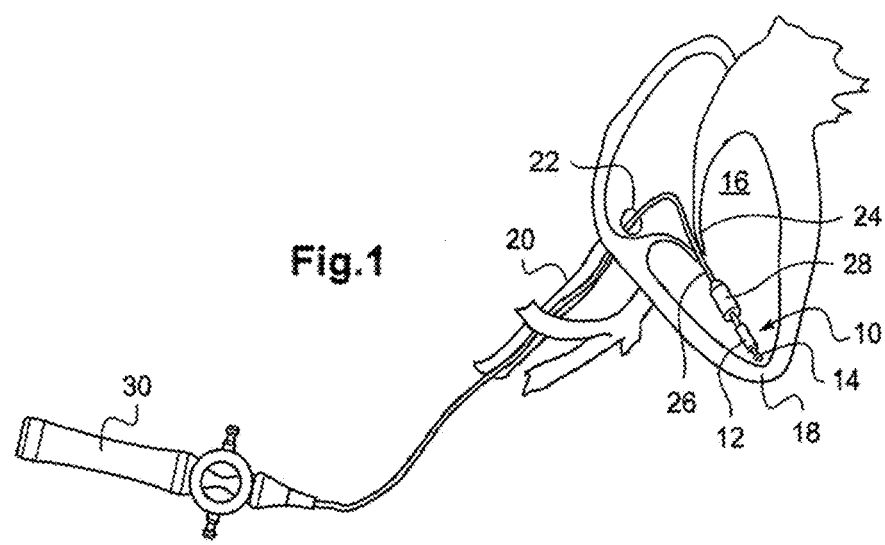
FIG. 1 is an overall view illustrating an implantation accessory coupled to a leadless capsule, in situation during an operation of implantation of this capsule into the right ventricle of a myocardium.
Figure 2:
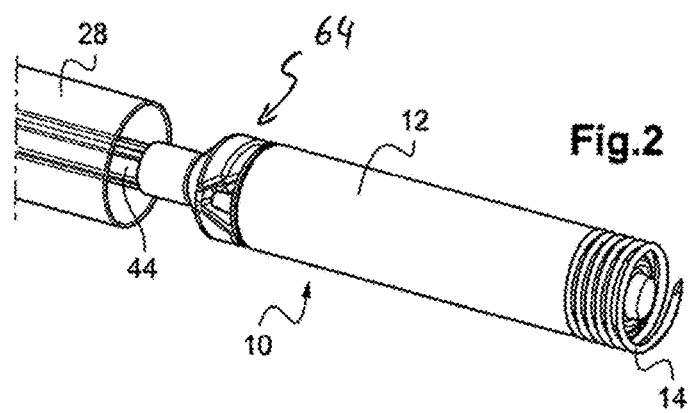
FIG. 2 illustrates a leadless capsule coupled to a catheter of the implantation accessory, extended out of a protective housing.

FIGS. 1 and 2 illustrate an implantation accessory coupled to a leadless capsule, in situation during an operation of implantation of this capsule into the right ventricle of a myocardium. FIG. 1 is a general overall view, and FIG. 2 shows an enlarged view of the leadless capsule, extended out of the protective housing located at the end of the implantation catheter.

The capsule, denoted 10, comprises in a per se known manner a tubular body 12 provided at one of its ends with a protruding helical anchoring screw 14 extending axially the tubular body 12 and rotationally integral with the latter. The anchoring screw comprises, in its distal portion, a length of the order of 1.5 to 2 mm of non-contiguous turns, adapted to enter the heart tissue for securing the capsule thereto.

Here and hereinafter, the term "proximal" (or "rear") will be considered with respect to the practitioner, i.e. on the free side of the handle, whereas the term "distal" (or "front") will refer to an opposite direction, hence directed towards the implantation site and the capsule. In the different figures appended, these proximal and distal directions correspond respectively to the left and the right. Likewise, the term "axial" will be used with reference to the axis of the handle, i.e. the greatest dimension of the latter, a "radial" direction being a direction located in the plane perpendicular to the axial direction.

In the illustrated example, the capsule is implanted in the right ventricle 16 of a heart, in the bottom of this ventricle in the region of the apex 18. Access to the right ventricle 16 is made through the vena cava 20, via the sinus 22, then the tricuspid valve 24, following a procedure well known per se and described for example in above-mentioned US 2014/0378991.

The implantation tool comprises for that purpose a guide catheter 26 with, at its distal end, a tubular protective housing 28 receiving the capsule, the latter being progressively extended out of the housing up to be docked to the heart wall. The protective housing 28 is adapted to receive the capsule, and in particular the anchoring screw 14, during the progression in the venous network, during the passage through the valve, etc., to protect the surrounding tissues from the potential risks of tearing by the screw before the latter reaches its definitive position.

At the opposite, proximal end, the catheter is connected to an operating handle 30 operated by the practitioner, which is the object of the present invention and which will be described in more detail with reference to FIGS. 5 to 24.

Figure 3:
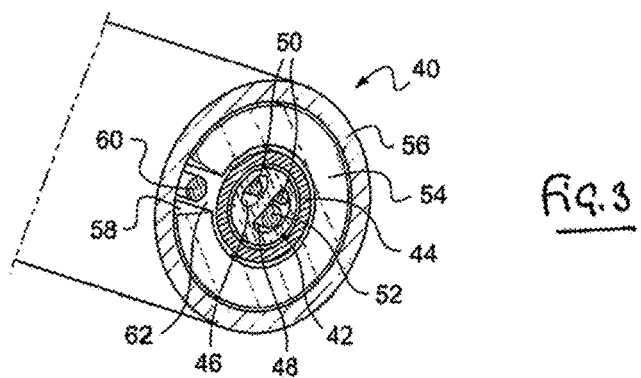
FIG. 3 is a cross-sectional view, along a radial plane, of a steerable catheter adapted to be operated by a handle according to the invention, showing the different elements of the internal structure of this catheter.
Figure 4:
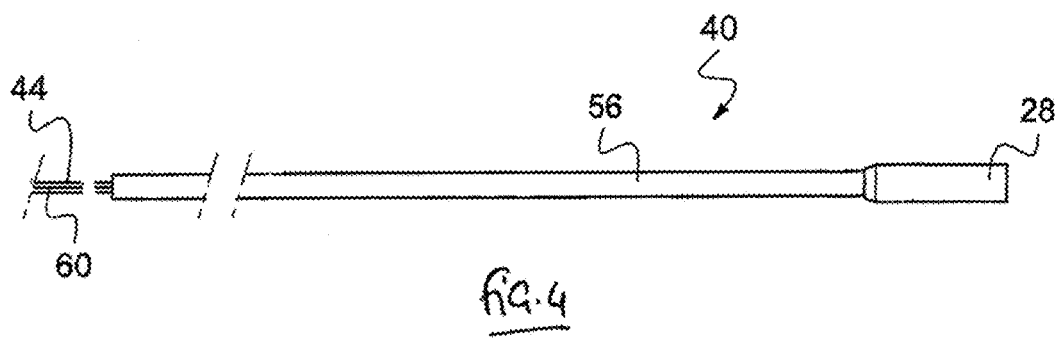
FIG. 4 is an overall top view of a catheter of FIG. 3, from its proximal end to its distal end.

FIGS. 3 and 4 illustrate an example of specific steerable catheter adapted to be operated by a handle according to the invention.

This steerable catheter 40 comprises a mobile internal tube acting as a delivery catheter. This mobile internal tube comprises a core 42 surrounded and protected by a envelop tube 44. The core 42 comprises central lumens, for example, in the illustrated example, two lumens 46, 48 serving for the passage of a security wire 50 and (optionally) a cable 52 for controlling an implantation tool located on the distal side.

The security wire is a flexible holding wire that remains, temporarily or definitively, connected to the capsule after the latter has been delivered at the implantation site and decoupled from the delivery catheter. It acts as an "Ariadne's thread" making it possible to find the capsule in order to direct again a catheter towards it in case of new intervention made necessary after a first non-satisfying electrical test at the initially reached implantation site.

The security wire 50 extends over the whole length of the catheter, with a first portion of the wire that, through the rear of the handle 30, enters the proximal end of the lumen 46, runs through the catheter along the whole length thereof until exiting through the lumen 46 on the distal side, forms a loop (for example about a ring or similar element on the rear of the capsule), then goes back through the other lumen 48 along the whole length of the catheter, in the reverse direction, up to the proximal end of the latter, where it exits at the rear of the handle 30, at the same place that the first end of the wire. The two ends of the security wire, which exit freely from the distal end, may be grasped at will by the practitioner, so as for him/her to be able, in case of need, to find out and explant a capsule already in place.

At its distal end (visible in FIG. 2), the mobile internal tube including the core 42 and the envelop tube 44 is fastened to a coupling member 64 for transmitting to the capsule the required movements of axial translation and rotation, imparted from the handle 30 on the proximal side. The mobile tube may hence act as a delivery catheter.

This internal tube 42, 44 is introduced into an intermediate external tube 54 with, inside the latter, a double degree of freedom in mutual rotation and in axial translation. The intermediate tube 54 is surrounded and protected by a sealed external sheath 56.

A longitudinal notch 58 is formed along the length and thickness of the intermediate tube 54.

More precisely, in the radial direction, the longitudinal notch 58 extends from the external surface of the envelop tube 44 up to the internal surface of the sealed external sheath 56, hence over the thickness of the external tube 54 (thickness that is, for example, of the order of 1.5 to 1.7 mm, typically of about 1.6 mm). In cross-sectional view, the longitudinal notch 58 extends over an angular sector of the order of 25 to 35°, typically about 30°.

The longitudinal notch 58 defines a space 62 housing a steering cable 60 that extends along the whole length of the catheter. On the proximal side, the steering cable 60 exits freely from the catheter and is connected, within the handle 30, to a mechanism (that will be described in detail with reference to FIGS. 17 to 24) that allows exerting from the handle a controlled axial traction to the cable 60. At its opposite, distal end, the cable is on the other hand fastened to the tubular protective housing 28. The traction so exerted to the cable 60 will result in generating a bending of the external tube 54 and hence of the catheter, mainly at the distal section, which is the most flexible.

More precisely, this bending of the catheter results from the fact that, on the one hand, the cable 60 is offset with respect to the axis of the catheter and that, on the other hand, the external tube 54 doesn't have a radially isotropic structure due to the presence of the notch 58. Hence, a more or less accentuated effort exerted on the cable 60 will result in tightening the latter (whose distal end is integral with the housing 12) and, by reaction, to bend the catheter approximately in a plane containing the notch 58 and the cable 60 in bent configuration. A longitudinal stiffness gradient of the external sheath allows obtaining a more accentuated bending on the distal side than on the proximal side and hence localizing the bending of the catheter in the area in which it is necessary.

The cross-section of the space 62 defined by the longitudinal notch 58 is moreover sufficient, after deducing the cross-section of the steering cable 60, to allow the free circulation of a flushing liquid injected from a flushing valve located near the handle 30, at the proximal end of the catheter. The flushing consists in injecting into the implantation site region a flushing liquid, or a contrast product making it possible to accurately follow the operation under an image intensifier.

Figure 5:
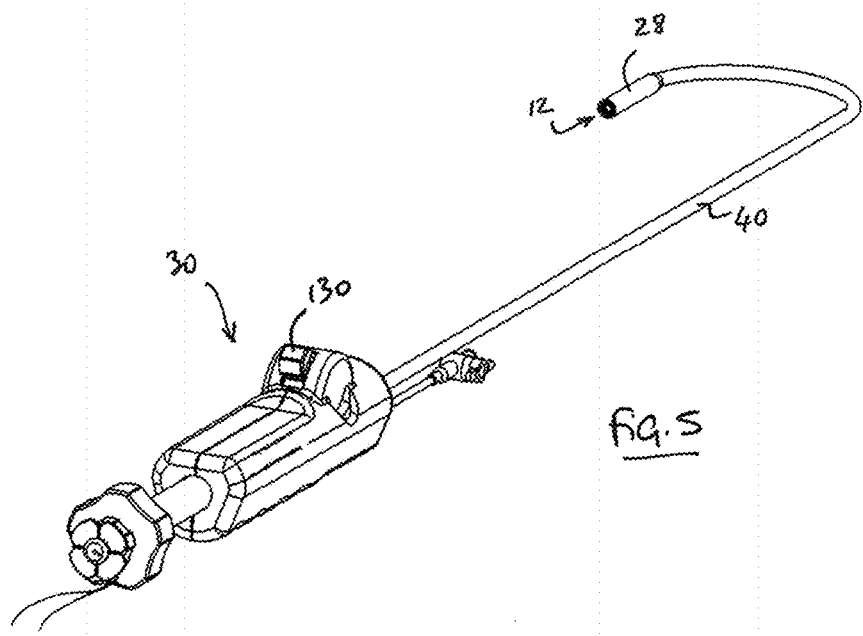
FIG. 5 is an overall perspective view showing the operation handle according to the invention, the specific catheter to which this handle is adapted, and, at the end of this catheter, a capsule ready for implantation, in an initial position in which it is still located inside its protective housing.
Figure 6:
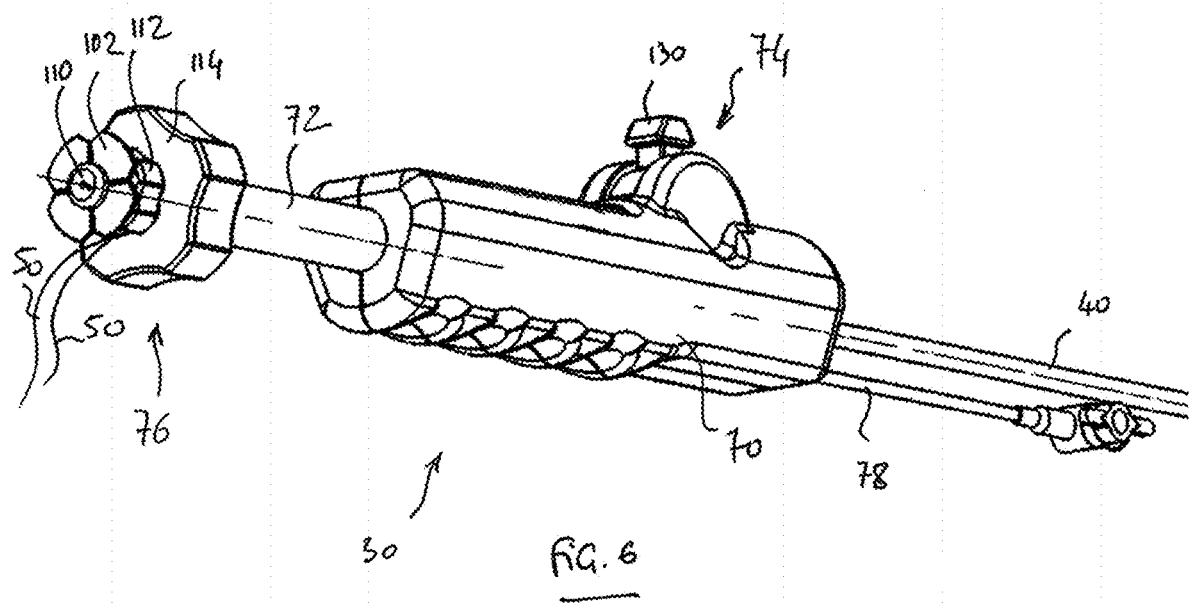
FIG. 6 is a perspective view showing in more detail the different elements of the handle of FIG. 5 that are accessible to the practitioner.

FIGS. 5 and 6 are overall views of the operating handle 30 according to the invention.

FIG. 5 shows more precisely the handle 30 with the specific steerable catheter 40 described hereinabove with reference to FIGS. 3 and 4, the handle 30 being mounted at the proximal end of this catheter 40. The distal end of the catheter 40 carries a ready-to-be-implanted capsule 12 that, in FIG. 5, is in an initial position in which it is still located inside the protective housing 28.

As illustrated in FIG. 6, the handle 30 is externally in the form of an external body 70 adapted to be grasped by one hand by the operator practitioner. The handle body 70 is integral in rotation and in translation with the external tube 54, 56 of the catheter 40.

On the proximal side of the handle body 70 emerges a rod of a piston 72 that is integral in rotation and in translation with the internal tube 42, 44 of the catheter 40. The piston 72 is mobile in rotation and in axial translation with respect to the handle body 70, so as to be able to remotely control, at the opposite distal end of the catheter 40, the exit of the capsule 12 out of the housing 28 (by a translational motion of the piston 72 with respect to the handle body 70), then the screwing of the capsule into the heart wall with the anchoring screw 14 (by an axial rotation motion of the piston 72 with respect to the handle body 70). The structure and operation of this piston will be described in more detail with reference to FIGS. 7 to 12 and 14 to 16.

The handle 30 is moreover provided with a first control mechanism 74 adapted to control the tension of the steering cable 60 located inside the catheter 40 and, consequently, the bending of the distal region of this catheter, said bending being visible in particular in FIG. 5. The structure and operation of this first control mechanism will be described in more detail with reference to FIGS. 17 to 24.

The first control mechanism 74 is advantageously arranged on the distal side of the handle body 70, which allows its direct operation by the thumb of the practitioner's hand holding the handle 30, the piston 72 being then operated in translation and rotation by the other hand with respect to the handle body 70.

At its distal end, the piston 72 carries a second control mechanism 76 for holding the security wire 50 in position and also adjusting the axial position of the latter with respect to the catheter internal tube 42, to maintain an approximately constant tension of this security wire 50 despite the bending variations applied to the catheter through the operation of the first control mechanism 74. The structure and operation of this second control mechanism 76 will be described in more detail with reference to FIGS. 12 to 14.

Finally, the handle comprises a flushing tube 78 in fluid communication with the internal lumens and interstitial spaces of the catheter 40 to allow the introduction of a flushing liquid (or a contrast agent), which will circulate along the catheter from the point at which it is introduced to the implantation site located at the distal end, at the housing 28. The particular structure of the coupling of the flushing tube 78 to the catheter 40 will be described in more detail hereinafter with reference to FIG. 11.

FIGS. 7 to 11 illustrate the different elements arranged inside the handle body 70.

The piston 72 slides inside a piston cylinder 80 between two extreme positions, i.e. a position of maximum extension (position illustrated in the different figures appended), corresponding to a configuration in which the capsule 12 is fully retracted inside the tubular housing 28, and an opposite position (not illustrated), in which the piston is maximally inserted into the handle body 70, corresponding to an arrangement in which the capsule 12 is fully extended out of the tubular housing 28.

Figure 7:
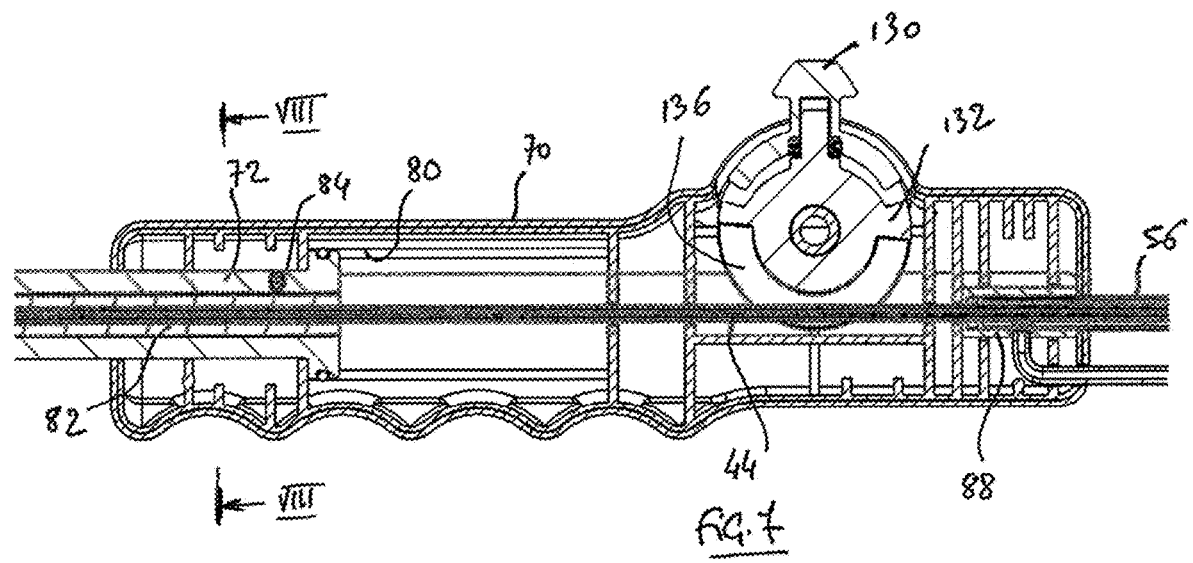
FIG. 7 is a sectional view, along a longitudinal plane, of the handle of FIG. 6.
Figure 8:
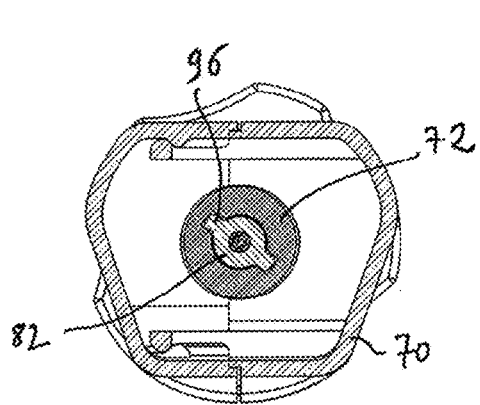
FIG. 8 is a cross-sectional view of the handle, along VIII-VIII in FIG. 7.
Figure 9:
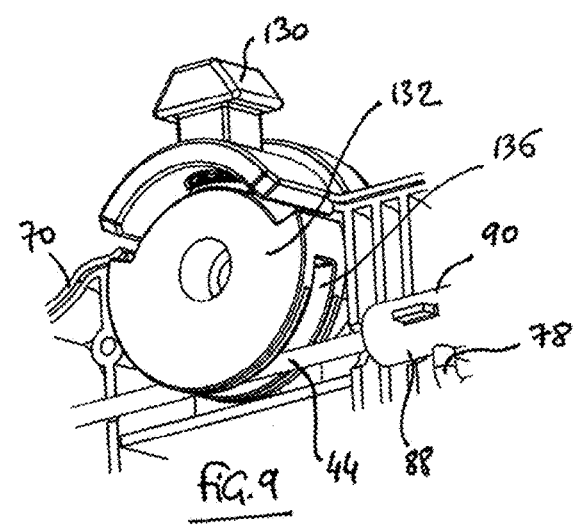
FIG. 9 is a cut-away perspective view of the distal part of the handle of FIG. 7, showing the control mechanism operable to control the steering of the catheter.
Figure 10:
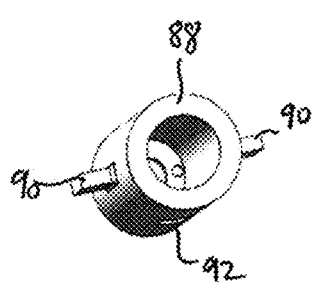
FIG. 10 is a detailed perspective view of the intermediate part for fastening the handle to the catheter external tube.

The piston 72 carries an internal tubular part 82 adhesively bonded to the proximal end of the steerable catheter internal tube 42, 44. The internal part 82 is inserted into an axial bore of the piston 72, to which it is fastened by a pin 84 (FIG. 7). The combined rotational and translational moves of the piston 72 can hence be identically transmitted to the catheter internal tube 42, 44, and, consequently, to the capsule 12 mounted at the opposite distal end of the latter.

Figure 11:
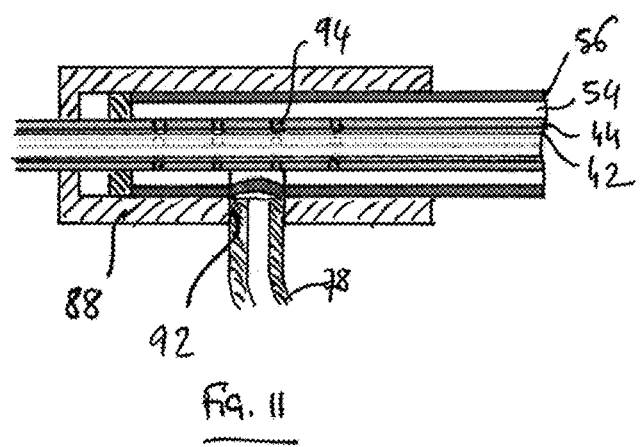
FIG. 11 shows in sectional view the detail of the interference between the part illustrated in FIG. 10 and the catheter proximal end, with in particular the flushing circuits.
Figure 12:
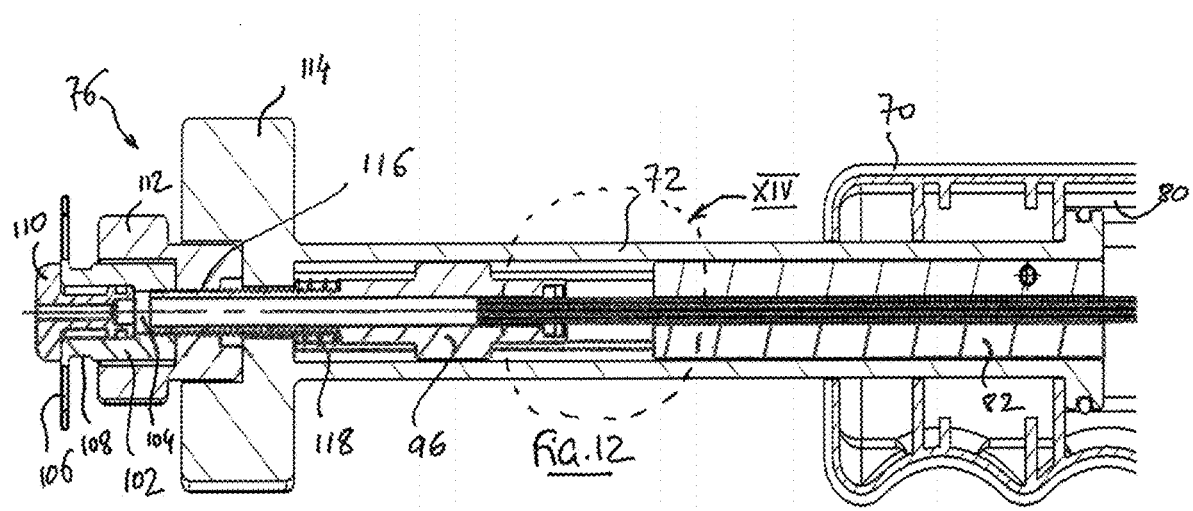
FIG. 12 is a sectional view of the handle of the invention at the proximal part of the latter, showing in particular the structure of the mobile piston and of the different elements are associated therewith.

As regards the catheter external tube 54, 56, the proximal end of the latter is adhesively bonded to an intermediate part 88 mounted in the handle body 70 at a distal end of the latter. The movements imparted to the handle body 70 by the practitioner's hand are hence transmitted identically to the catheter external tube 54, 56. The intermediate part 10, shown in isolation in FIG. 10, includes lateral protrusions 90 that prevent it from rotating with respect to the handle body 70. It moreover comprises a radial orifice 92 sealingly connected to the flushing tube 78. As illustrated in FIG. 11, this orifice allows putting the fluid of the flushing tube 78 in communication with the space remaining between the internal tube 42, 44 and the external tube 54, 56, and hence with the longitudinal notch 58 (FIG. 3), which allows the progression of the fluid to the implantation site. Moreover, holes 94 formed into the catheter internal tube allow the passage of the flushing fluid also into the catheter internal central lumens 46, 48 (FIG. 3).

The structure of the different elements carried by the piston 72 and constituting in particular the second control mechanism 76 adapted to control the security wire 50 will now be described with reference to FIGS. 12 to 16.

The piston 72, which is hollow, houses a slider 96 that is mobile with respect to the piston according to a single degree of freedom in axial translation. On the other hand, it is rotationally integral with the piston 72, so that any rotational movement imparted to the latter is identically transmitted to the slider 96. At its distal end, as more particularly illustrated in the detailed cross-sectional view of FIG. 14, the slider 96 is made rotationally and translationally integral with the mobile tube 42, 44 of the steerable catheter 40. More precisely, a silicone washer 98 ensures a radial seal, and a ring 100 fastens the slider 96 to the catheter envelope tube 44, for example by adhesive bonding. The lumens 46, 48 of the mobile tube core 42 are left open at the proximal end of the catheter, which allows the two strands of the security wire 50 to emerge from these lumens up to the internal space of the slider 96, from which their then emerge at the most proximal end of the latter, to extend freely out of the handle, as can be seen in the perspective views of FIGS. 5 and 6.

Figure 13:
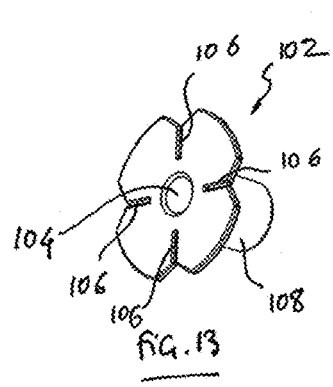
FIG. 13 is a detailed perspective view of the part located at the proximal end of the piston and serving to fasten the security wire.
Figure 14:
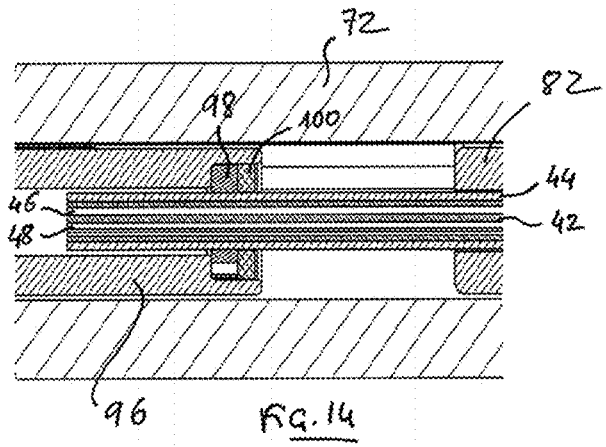
FIG. 14 shows in sectional view the detail, denoted XIV in FIG. 12, of the interface between the piston and the catheter internal tube.

To block in position the two strands of the security wire 50, the second control mechanism 76 comprises a holding member 102 mounted on the side 96 at the proximal part of the latter. The holding member 102, illustrated in isolation in FIG. 13, is in the form of a cylindrical part passed through by a threaded axial bore 104 and ended by a flat portion carrying one or several radial slots 106 (four slots in the illustrated example). The width of the slots 106 is slightly higher than the diameter of the security wire, so as to be able to insert into either one of these slots the two strands of this wire that emerge from the bore 104. The free end of the strands is wound around the tubular core 108 of the holding member 102, that forms a coil. The security wire is secured at its final position by insertion of a silicone plug 110 into the bore 104, so that, after this operation, there will no longer exist any possibility of sliding or displacement of the security wire with respect to the side 96, to which the security wire will hence be fastened. The silicone plug 110 also ensures the seal of the inner volume of the slider 96 with respect to the outside, volume into which the lumens 46, 48 open.

The control mechanism moreover comprises a system for adjusting the relative axial position of the security wire with respect to the internal tube 42, 44 (a tube that is itself integral with the slider 96), and hence for adjusting the tension of the security wire in this internal tube, whatever the conformation and the bending given to this tube during the different approach operations performed during the progression within the venous network and the heart chambers.

This adjustment system comprises a wheel 112 axially interposed between the holding member 102 and a central housing of a button 114 formed at the proximal end of the piston 72, a rotational degree of freedom remaining with respect to each of these two elements. The wheel 112 is screwed on a hollow threaded rod 116 (to let the security wire pass through) formed at the proximal end of the slider 96, the holding member 102 being screwed at the end of this threaded rod 116. Moreover, a return spring 118 stresses the slider in the axial direction to avoid any clearance with the piston body 72.

Thanks to this arrangement, a relative rotation of the wheel 112 with respect to the button 114 of the piston 72 results in modifying the relative axial position of the holding member 102, hence of the security wire, with respect to the piston 72, and hence with respect to the catheter internal tube 42, 44, by axial translation of the slider 96 in one direction or in the other. It is hence possible to finely adjust the axial position of the security wire, and hence the tension thereof, which allow in particular the capsule 12 to be maintained in any circumstances perfectly secured inside the tubular housing 28 located at the opposite, distal end of the catheter (FIG. 5) during the whole phase of introduction of the capsule into the venous network up to the final implantation site.

Figures 15, 16:
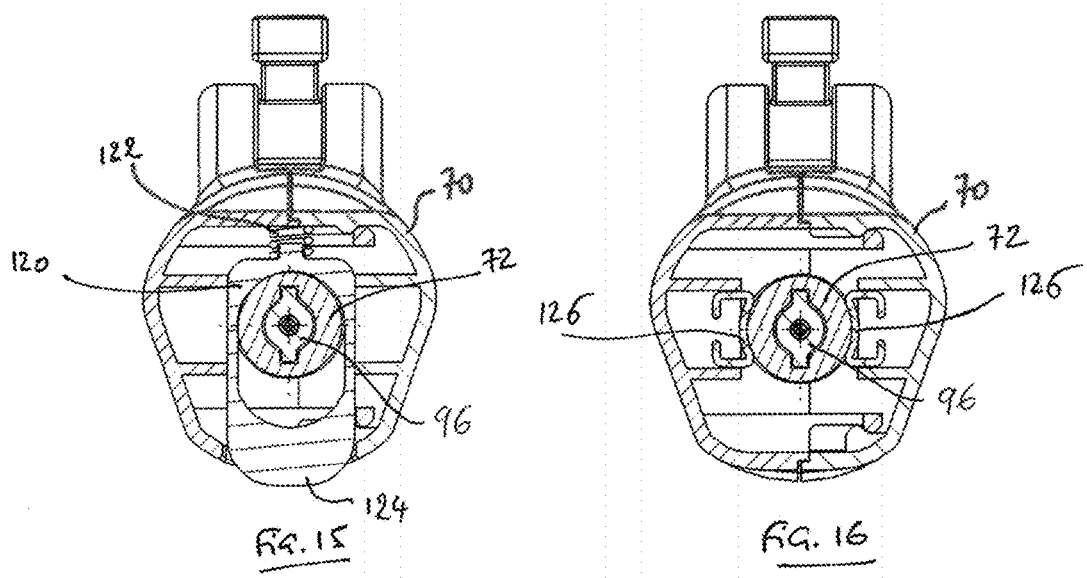
FIG. 15 is a cross-sectional view taken at the proximal part of the handle, illustrating an example of device for blocking the piston in position.
FIG. 16 is a cross-sectional view taken at the proximal part of the handle, illustrating another example of device for blocking the piston in position.

Moreover, the handle advantageously comprises a mechanism for securing in an unlockable manner the piston 72, and hence the internal tube 42, 44 of the catheter, to the handle body 70, and hence to the external tube 54, 56 of this same catheter. The two catheter tubes must indeed remain fastened to each other during the whole phase of approach, until the moment of extension of the capsule out of the tubular housing 28 (by translation of the piston 72), then of screwing thereof at the implantation site (by rotation of the piston 72). This unlockable mechanism may for example comprise, as illustrated in FIG. 15, a transverse beam 120 stressed by a spring 122, bearing against the external surface of the piston 72 with a friction that is sufficient to obtain the desired effect. The beam 120 includes an emergent portion 124 in the form of a button that the practitioner can press when needed to unblock the mechanism and release the piston 72 with respect to the handle body 70.

FIG. 16 illustrates a variant of this mechanism implementing friction parts 126 exerting an axial effort to the external surface of the piston 72 and preventing the latter from moving in rotation and in translation under a certain threshold of effort exerted by the practitioner on the piston 72.

Various embodiments of the first control mechanism 74 for controlling the steering of the catheter from the handle will now be described with reference to FIGS. 17 to 24.

In all the embodiments illustrated, the mechanism is controlled by a lever 130 arranged at the distal part of the handle (as can be seen in FIGS. 5, 6, 7 and 9) that the practitioner can for example control with the thumb of the hand that holds the handle. This lever 130 is integral with a drum 132 to which is fixed the steering cable 60 emerging from the longitudinal notch 58 (FIG. 3) made along the intermediate tube 54. The cable 60 being connected, at its distal end, to the external tube of the catheter, a traction exerted to this cable will result in a bending of the catheter in its most flexible portion, generally the distal end portion. That way, a forward or rearward push on the lever 130 will result in more or less strongly tightening the steering cable, and consequently, to create a more or less important bending, in one direction or in the other, of the distal end of the catheter.

The steering cable is mounted at the periphery of the drum 132 to which it is fixed, for example by crimping and/or laser welding. The drum is moreover provided, on a portion of its periphery, with a groove 136 letting the catheter internal tube 42, 44 pass through, for the connection of the latter with the piston 72 at the proximal portion of the handle, as described hereinabove (the catheter external tube 54, 56 being for its part made integral with the handle body 70 by means of the above-described intermediate part 88, in a region located at the distal end of the handle). The drum 132 is rotationally mobile about a transverse axis 134 perpendicular to the longitudinal axis of the handle and radially remote from the latter.

Once the bending adjusted to the desired shape, the drum 132 shall be blocked in position so that the practitioner can release the lever 130.

Figure 17:
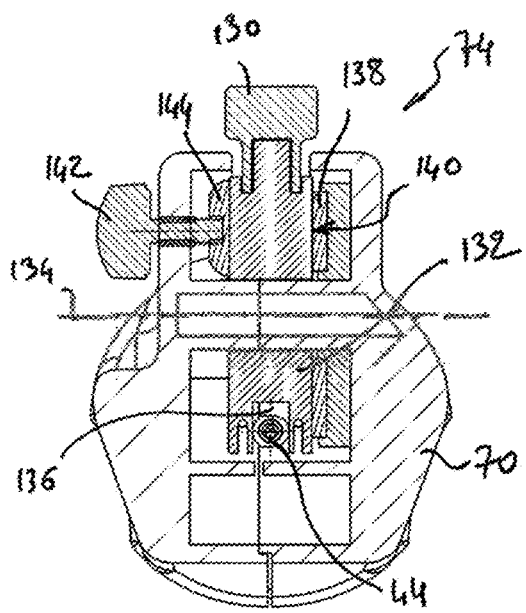
FIG. 17 is a sectional view taken at the distal part of the handle, illustrating a first example of device for blocking the bending actuator in position.
Figure 18:
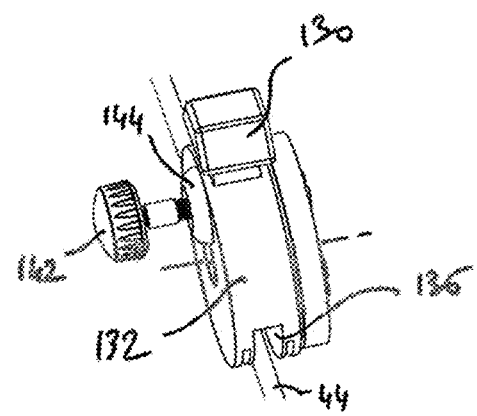
FIG. 18 is a perspective view of the actuator blocking device, viewed in isolation.
Figure 19:
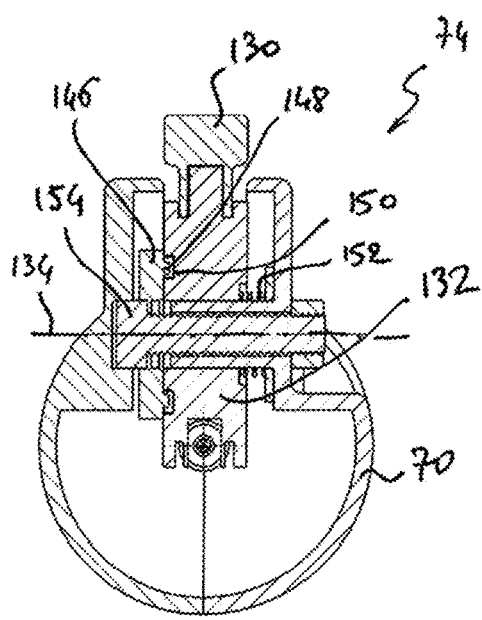
FIGS. 19 and 20 are equivalent to FIGS. 17 and 18, for a second exemplary embodiment.
Figure 20:
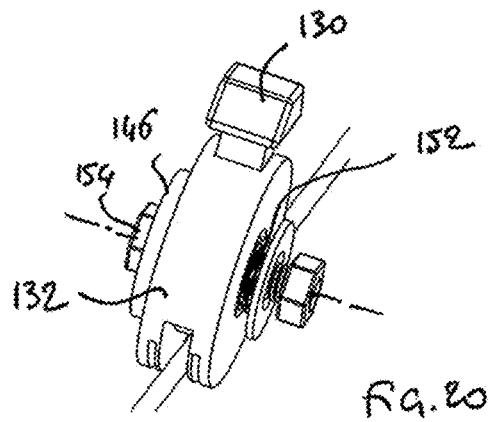
Figure 21:
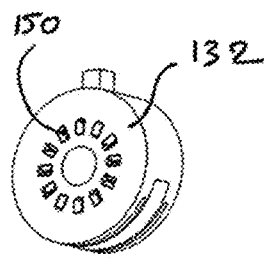
FIGS. 21 and 22 are perspective views of the two cooperating parts, viewed in isolation, serving for the indexing of the actuator blocking device of FIGS. 19 and 20.
Figure 22:
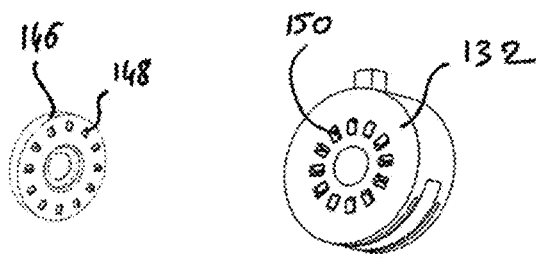

For that purpose, in a first embodiment illustrated in FIGS. 17 and 18, a ring 138 made of a friction material, for example silicone, bears against one of the faces 140 of the drum 132. To maintain this pressure, a stop button 142 is screwed into the handle body 70 and carries a pressure member 144 pressing against one face of the drum 132 that is opposite to the face 140.

FIGS. 19 to 22 illustrate a second embodiment, in which the rotation of the drum 132 is indexed by a toothed wheel 146 carrying protrusions 148 circumferentially distributed at regular intervals on one of its faces, these protrusions 148 cooperating with counterparts recesses 150 formed opposite to them in the drum 132. In order for the friction of the protrusions 148 to oppose to the traction force of the steering cable, a spring 152 acts in the direction of the axis 154 on a mobile part whose head bears against the toothed wheel 146, hence immobilizing the latter in the chosen indexing position.

FIG. 23 illustrates a third embodiment, implementing planar surfaces having different slopes with respect to the axis 134, with a first inclined plane 156 integral with the handle body 70, and a second inclined plane 158 integral with a stop button 160 mobile in rotation about the axis 134. Due to the opposite slopes of these surfaces, a rotation, for example by half a turn or a quarter of a turn, of the button 160 will result in axially displacing a disk-shaped part 166 acting as a brake and carrying for example a circular seal 164 made of a friction material, coming in rest against a lateral face 166 of the drum 132. Hence, in a first position of the stop button 160, the lever 130 is freely operable and can be adjusted to the chosen position, then a rotation of the stop button 160 to a second position will block this adjustment by pressing and blocking the part 162 against the drum 132.

FIG. 24 illustrates a fourth embodiment, in which the friction force allowing blocking the lever in position is exerted by a mobile part 168 radially pushed against an internal face 170 of the handle body 70 in the vicinity of the lever 130 under the effect of a spring 172. To move the lever 130, the practitioner will have to radially press the latter (with respect to axis 134); after having found the position corresponding to the desired bending for the catheter, he/she will just have to release the radial pressure on the lever 130 to immobilize and block the latter, and consequently the drum 132 and the steering cable, in the obtained configuration.

A clinical procedure of implantation of an intracorporeal capsule by means of a tool comprising the just-described operating handle will now be explained.

The preparatory phase of the implantation consists in puncturing the femoral or jugular vein and making an introducer and a dilatator progress on a guidewire up to the atrial region. The dilatator and the guidewire are then removed and the delivery tool (the unit formed by the steerable catheter, the capsule located in the housing at the distal end, and the handle according to the invention at the proximal end) is moved forward into the heart chamber through the tricuspid valve up to the target zone of implantation (apex of the right ventricle or intraventricular septum), until reaching the configuration illustrated in FIG. 1 in the case of a target zone located at the apex 18 of the right ventricle 16.

To reach this position, the end of the catheter may be bent in the desired manner, in particular at the time of passing through the atrium, by operation of the lever 130 of the first control mechanism 74.

Pushing this lever 130 forward or rearward will result, as explained hereinabove, in bending the distal portion of the catheter 40 (as in the configuration illustrated in FIG. 5), in one direction or in the other, to be able to accurately direct the housing 28 (with the leadless capsule 12 located inside) towards the ventricle and to allow in particular the passing through the tricuspid valve 24.

During this bending operation, the security wire that runs through the catheter over the whole length thereof has its tension modified, increased or released according to the direction in which the catheter end is directed.

To compensate for this tension modification, the practitioner acts on the wheel 112 for tensioning the security wire 50, in one direction or the other, so that this wire remains under tension, in particular a tension sufficient to maintain the leadless capsule 12 suitably docked to the coupling interface 64 of the distal end of the mobile tube 44 of the catheter 40.

Once the desired accurate direction obtained, the practitioner blocks the lever 130 in the desired position through one of the various mechanisms that have been exposed with reference to FIGS. 17 to 24 (stop button 142 or 160, indexing by the toothed wheel 148, pressure on the lever 130, etc.). If, for any reason, it is required to bring the catheter 40 back to its rectilinear position, or to reduce the bending of its distal end, the practitioner will just have to release the lever 130 and to bring it back to its initial position.

Once the final configuration reached, with the housing 28 brought to the implantation site chosen, the security wire is unblocked by removing the silicone plug 110 and unfastening the two wire strands from the holding member 102 to which they were attached.

The practitioner then extends progressively the leadless capsule 12 out of the housing 28 by pushing the piston 72 in axial translation with one hand, the other hand holding immobile the handle body 70 that is integral with the external tube of the catheter 40 and hence of the housing 28. The leadless capsule will then be progressively extracted from the housing 28, until being docked to the myocardium wall. The practitioner then imparts a rotational move to the capsule to screw and anchor the latter into the wall, this move being obtained by a rotation exerted on the piston 72 by the hand holding this piston, the other hand continuing to maintain immobile the handle body 70.

The capsule is advantageously coupled to the internal tube of the catheter 40 by a system (denoted 64 in FIG. 2), with automatic torque limitation, so as to avoid any tearing of the tissues that would result from a core drilling effect by the anchoring screw 14. The rotation of the piston 72, and hence of the capsule 12, is continued until its front face, that carries an electrode, bears against the wall. From this position, which is in principle the definitive position of the capsule, the practitioner may then uncouple the catheter from the capsule by unblocking the security wire.

The good anchoring of the capsule and the efficiency of the implantation site chosen are then tested by per se known procedures: visual examination by fluoroscopic control, electrical controls (excitation threshold, impedance measurement, etc.), evaluation of the ECG signal collected by the capsule and transmitted to an external programmer.

If a repositioning of the leadless capsule turns out to be necessary following these controls, the practitioner will execute the following successive steps:

exerting a traction on the security wire 50 to bring the capsule closer from the housing 28;

reintroducing the capsule into the housing by a slight traction exerted on the piston 72, and simultaneous moving the handle body 70 forward so as to realign the capsule with the housing, until the capsule is full retracted into the housing 28 and coupled again to the catheter internal tube 42, 44 by the interface member 64;

blocking the security wire 50 by rotating the wheel 112 and locking again the security wire by means of the holding member 102 blocked by the silicon plug 110;

unscrewing the capsule by rotating the piston 72 with respect to the handle body 70;

extending the capsule again to another implantation site by the procedure exposed hereinabove and reevaluating the fixation and the electric performances.

Once the definitive implantation site verified, the emerging portion of the security wire 50, on the proximal side thereof, is cut near the wheel 112, then the wire is fully removed, by traction on one of the two strands. The steerable catheter, as well as the introducer, can then be removed.

After hemostasis of the venous access, the operating parameters suitable for the patient are programmed in the capsule by telemetry, via a wireless communication link.

The invention claimed is:

1. An operating handle capable of being mounted at a proximal end of a steerable catheter for the implantation of an intracorporeal capsule, the catheter comprising an internal tube and an external tube, coaxial to each other, mounted telescopically into each other, with possibilities of mutual rotation and mutual axial translation, the internal tube comprising at least one central lumen extending from the proximal end to a distal end of the catheter, the at least one lumen housing a security wire moving freely in the lumen, the internal tube being coupled in translation and in rotation at its distal end to the intracorporeal capsule, the catheter further comprising, over the length of the external tube, at least one steering cable adapted to undergo a traction exerted from the proximal end of the catheter, the traction exerted on a single one of said at least one steering cable generating in a given plane a bending of a corresponding distal region of the catheter, wherein the operating handle comprises:

a handle body adapted to be held in hand by an operator, the handle body being coupled to the external tube of the catheter;

a piston, axially mobile in rotation and in translation inside the handle body, and coupled in rotation and in translation to the internal tube of the catheter; and a first control mechanism, comprising a bending actuator operable to modify in a controlled manner a tension of said single one steering cable, wherein said single one steering cable is offset with respect to the internal tube, wherein said first control mechanism comprises a drum to which is fixed said single one steering cable, said drum being rotationally mobile about a transverse axis radially offset from a longitudinal axis of the operating handle, and wherein said bending actuator is integral with said drum and operable to control a rotation of the drum for winding said single one steering cable for modifying in a controlled manner the tension of the single one steering cable for controlling said bending of the distal region of the catheter in the given plane by said controlled tension, with no relative displacement of a pair of cables operated in opposition.

2. The operating handle of claim 1, further comprising:
a second control mechanism, comprising a member for holding the security wire and a member for adjusting a relative axial position of the security wire with respect to the internal tube of the catheter, whereby keeping the security wire in a tight condition is irrespective of a bend given to the catheter by operating the first control mechanism.

3. The operating handle of claim 2, wherein the second control mechanism comprises a slider mobile in translation inside the piston, comprising at its distal end a device for fastening it to the proximal end of the catheter internal tube, and further comprises a device for adjusting the axial position of the slider inside the piston.

4. The operating handle of claim 3, wherein the device for adjusting the axial position of the slider inside the piston comprises a threaded rod and a wheel mobile in axial rotation with respect to the piston, the wheel comprising a threaded bore into which is mounted the threaded rod.

5. The operating handle of claim 4, wherein the slider, the threaded rod and the wheel are mounted coaxially to each other and are passed through by a common axial orifice opening on a proximal side of the handle and from which emerges a portion of the security wire extending beyond the operating handle.

6. The operating handle of claim 5, wherein the security wire holding member is located at an exit of the common axial orifice, on the proximal side of the handle.

7. The operating handle of claim 3, further comprising an axial backlash compensation device between the slider and the piston.

8. The operating handle of claim 2, wherein the first control mechanism comprising the winding drum and the bending actuator is arranged on a distal side of the handle body, and the second control mechanism, comprising the security wire holding member and the security wire adjustment member, is arranged on a proximal side of the handle body, and the piston comprises, at its proximal end, an operating button protruding from the handle body on the proximal side of the handle body.

9. The operating handle of claim 1, wherein the first control mechanism further comprises a mechanism for locking a position of said rotation of the winding drum, and a device for blocking/unblocking-said mechanism for locking, adapted to be controlled by an external action from the operator.

10. The operating handle of claim 9, wherein, in an absence of external action from the operator, the blocking/unblocking device is maintained in a blocked position.

11. The operating handle of claim 9, further comprising a mechanism for indexing said position of said rotation of the winding drum controlled by the bending actuator.

12. The operating handle of claim 1, further comprising at least one access pathway in fluid communication with an inside of the catheter for the circulation of a flushing liquid along a catheter flushing pathway comprising the at least one central lumen.

13. The operating handle of claim 1, further comprising a mechanism for rotationally blocking the piston with respect to the handle body, the blocking mechanism being adapted to be actuated by an operator of the handle, the blocking mechanism being operational between a blocking configuration, in an absence of external action exerted by the operator, and an unblocking configuration, under an external action exerted by the operator.

* * * * *